United States Patent [19]

Coleman et al.

[11] Patent Number: 4,690,671
[45] Date of Patent: Sep. 1, 1987

[54] LUBRICATED TAMPON INSERTER

[76] Inventors: Mary T. Coleman, 23 Mertensia La., Henrietta, N.Y. 14467; Hedy E. Tasbas, 29 Northfield Gate, Pittsford, N.Y. 14534

[21] Appl. No.: 787,470

[22] Filed: Oct. 15, 1985

[51] Int. Cl.[4] .............................................. A61F 13/20
[52] U.S. Cl. ....................................... 604/12; 604/14; 604/15
[58] Field of Search ....................... 604/11, 12, 15, 16, 604/18, 904, 287, 288

[56] References Cited

U.S. PATENT DOCUMENTS

| | | | |
|---|---|---|---|
| 2,739,593 | 3/1956 | McLaughlin | 604/15 |
| 3,139,886 | 7/1964 | Tallman et al. | 604/12 |
| 3,335,726 | 8/1967 | Maranto | 604/12 |
| 3,674,025 | 7/1972 | Bleuer | 604/12 |
| 3,717,149 | 2/1973 | Morane | 604/14 |
| 3,791,385 | 2/1974 | Davis et al. | 604/12 |
| 4,026,292 | 5/1977 | Hutchins et al. | 604/904 |
| 4,421,504 | 12/1983 | Kline | 604/12 |

*Primary Examiner*—C. Fred Rosenbaum
*Assistant Examiner*—Denise Whelton
*Attorney, Agent, or Firm*—Robert M. Phipps

[57] ABSTRACT

The insertion and removal of tampons from a body cavity is facilitated by the use of an inserter equipped with a moveable and removable fluid reservoir at the place of tampon exit and conduits which carry a portion of the fluid to the other end of the tampon. The fluid can be a lubricant, a medicant or a combination thereof.

14 Claims, 4 Drawing Figures

LUBRICATED TAMPON INSERTER

BACKGROUND

1. Field of the Invention

This invention relates to a device and its use in inserting tampons into a body cavity.

2. Description of the Prior Art

The use of tampons to absorb various fluids in the cavities of the body is well known. However, the absorbent nature of the tampon makes it difficult to move into and retrieve from these cavities. Various types of appliances have been, in the past, provided for applying lubricant, e.g., petroleum jelly, cold cream, to the surface of the vaginal canal to obviate irritation. However, it was found difficult to release the lubricant and apply the same to the wall of the vaginal canal without accidental displacement or spillage and waste of lubricant.

In U.S. Pat. No. 3,335,726 (1967) L. M. Maranto disclosed inserting at the exit end of a tampon inserter tube a storage chamber for lubricant through which the tampon, at the time of insertion into the body cavity, had to be pushed. However, only the leading end of the tampon was lubricated when the tampon was pushed out of the tube.

In U.S. Pat. No. 3,717,149 (1973) B. P. Morane disclosed a pack for catamenial tampons in which the end of the injector to be inserted in the vagina and corresponding end of the tampon are coated with a lubricant. While the injector device was different from Maranto's device, the results with the tampon were substantially the same.

E. K. Davis, et al, in U.S. Pat. No. 3,791,385 (1974) disclosed placing a tampon within a collapsible monocoque shell of ovular form and then inserting it into the vagina. The shell arrangement was to provide an effective seal with the vagina walls. The shell also eliminated direct contact between the tampon and the mucus membrane. However, removal of the shell created a partial vacuum which necessitated a valve arrangement to equalize air pressure between the vaginal vault and the atmosphere.

More recently in U.S. Pat. No. 4,421,504 (1983) L. H. Kline disclosed a device for placing an object, including a tampon, in a body cavity. Lubricant is formed out through holes in the sides of the inserter, then the inserter is placed in the cavity and finally the object is forced through the remaining lubricant and out the end of the inserter into the cavity. Kline is primarily directed to inserting supositories and does not consider the problem of removing tampons.

Among the objects of the invention is the easier removal of tampons from a body cavity. Another object is the convenient means of applying controlled amounts of lubricants and medicants to tampons. Still another object is the continued application of a topical medicant to the surface of a body cavity. These and other objects will be apparent to those skilled in the art upon the reading of this specification.

SUMMARY OF THE INVENTION

In accordance with this invention these is provided a device for placing an absorbent tampon into a body cavity comprising (a) an applicator body comprising a tubular-like body within which said tampon in placed, said tubular-like body containing a plurality of conduits extending longitudinally along the inner side of said tubular-like body whereby fluid can be conducted down the side of said tubular-like body from one end of said tampon to and on to the other end of said tampon, (b) a fluid reservoir moveably and removeably attached to one end of said applicator body, and (c) movement means, moveably secured within said applicator body and at the end opposite said fluid reservoir, sized and shaped to fit within said applicator body, wherein said movement means can move the tampon out of the applicator body when the device is used, whereby when said device is placed within the body cavity the treated tampon can be moved into said body cavity.

DESCRIPTION OF THE PREFERRED EMBODIMENTS

Figure 1:
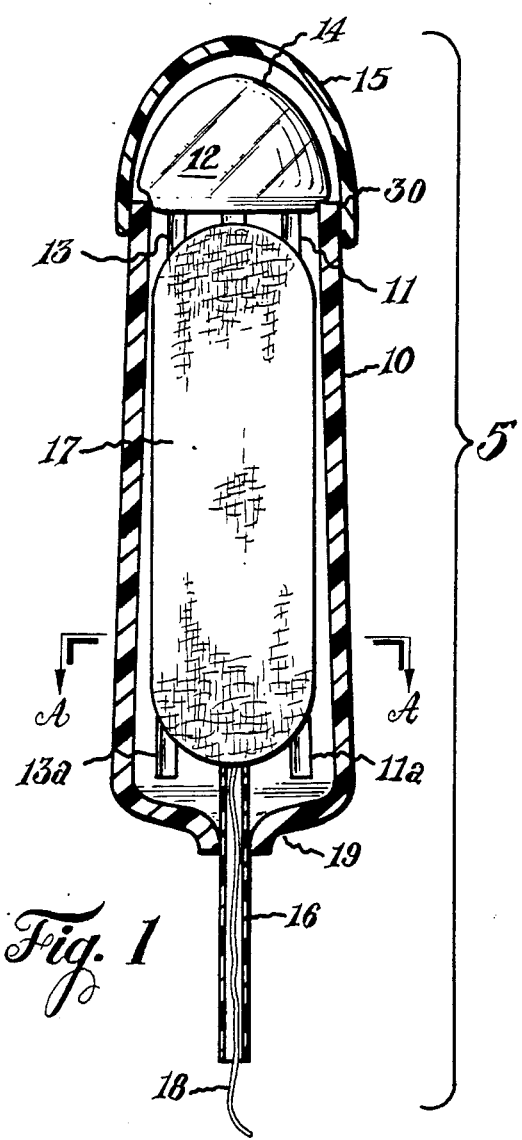
FIG. 1 is a longitudinal sectional view of the inserting device of this invention with tampon wherein the conduits are grooves.

One embodiment of the tampon inserter device 5 of the invention is shown in FIG. 1. In this embodiment the inserter device 5 has an applicator body made up of a tubular body 10 which has on its inner surface a plurality of groove conduits 11, 12, 13, etc. Tubular body 10 is of sufficient diameter to receive tampon 17 and permit its ejection without undue force by use of plunger 16. In a conventional manner the tampon removal string 18 passes through the longitudinal opening of plunger or piston 16. Tubular body 10 can be reduced in diameter, or necked down, at one end 19 so as to provide means for positively retaining in place plunger 16. To the mouth or open end 30 of tubular body 10 is fitted an easily ruptured and removed fluid reservoir 14. (The reservoir can be mechanically or frictionally held in place at mouth 30 as desired.) Reservoir 14 is frictionally head against the inside of tubular body 10. To aid in the release of the fluid reservoir 14 is so constructed that it will preferentially rutpure and empty into tubular body 10. Reservoir 14 is shielded against premature discharge force by the use of a removable reservoir cap 15. As a shield only cap 15 may be made from a rigid or pliable material as desired. As shown in FIG. 1 the groove conduits 11, 12, 13 etc., extend substantially the full length of tubular body 10.

Figure 2:
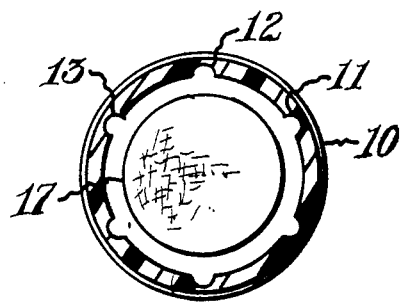
FIG. 2 is a cross sectional view of the device of FIG. 1 along line A—A.

The cross section, along line A—A in FIG. 1 of inserter device 5, as shown in FIG. 2 further shows the nature and placement of groove conduits 11, 12, 13, etc. The actual number, size and placement of groove conduits 11, 12, 13, etc., is a matter of choice in view of the lubricant or medicant fluid to be used in reservoir 14. The conduits can be varied in shape by well known techniques employed in plastic molding and extrusion technologies. The conduits 11, 12, 13, etc., for instance, may have a cross section resembling a V, an inserted V, an U of a continous corrugated surface. Additionally, these conduits can be formed by ribs or lands as a part of the extrusion process for preparing the tubular body 10.

Figure 3:
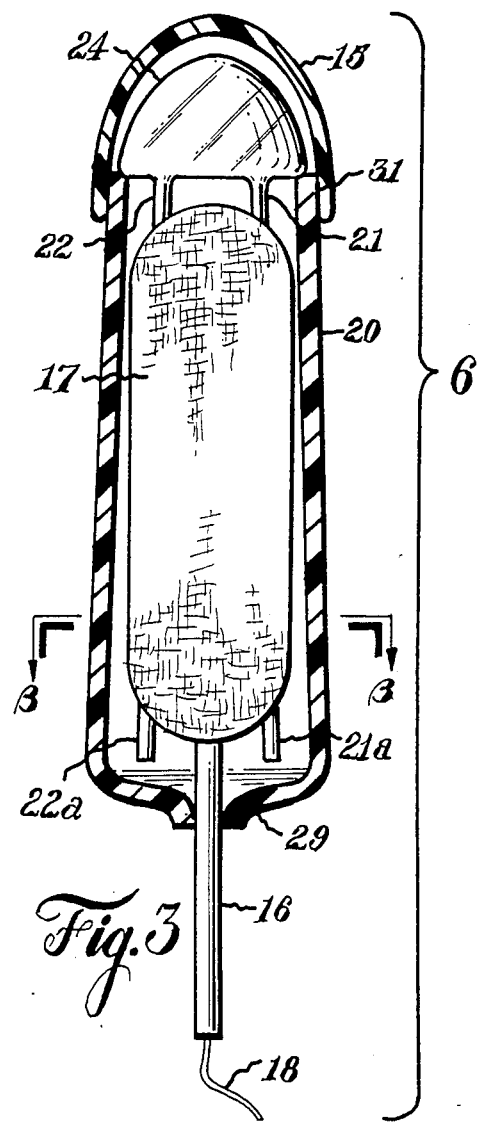
FIG. 3 is a longitudinal sectional view of a variant of the inserting device of this invention containing a tampon wherein the conduits are tubes.

Another embodiment of the tampon inserter device 6 of this invention is illustrated in FIG. 3. In this embodiment inserter device 6 has an applicator body made up of a tubular body 20. The tubular body 20 is of sufficient diameter to receive tampon 17 and tube conduits 21, 22, etc., while permiting ejection of tampon 17 without undue force by use of plunger 16. Tubular body 20 can be reduced in diameter, or necked down, at one end 29 so as to provide means for positively retaining in place plunger or piston 16. In a conventional manner tampon removal string 18 passes through the longitudinal opening of plunger 16. Tubular body 20 may be tapered slightly inwardly at mouth 31 to assist insertion of tubular body 20 into the desired body cavity.

At the mouth or open end 31 of tubular body 20 is located an easily ruptured and removed fluid reservoir 24. Tube conduits 21, 22, etc., are connected to reservoir 24. The reservoir 24 is shelded against premature discharge force by the use of removeable reservoir cap 15.

Figure 4:
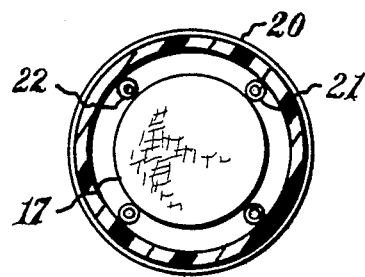
FIG. 4 is a cross sectional view of the device of FIG. 3 along line B—B.

The cross-section along line B-B in FIG. 3 of inserter device 6 as shown in FIG. 4 further shows the nature and placement of tube conduits 21, 22, etc. The actual number, size and placement of tube conduits is a matter of choice taking into consideration the nature of the medicant and or lubricant fluid to be used in reservoir 24. Alternatively tube conduits 21, 22, etc., can be formed at the time tubular body 20 is prepared or these conduits can be separately made and permanently attached to tubular body 20 by the use of adhesives or heat as desired. In such cases the reservoir will then be like reservoir 14 of FIG. 1.

In one aspect of this invention fluid reservoir 24 and tube conduits 21, 22, etc. together with the lubricant-/medicant fluid not shown, can be prepared as an unitized package by current technology well known in the packaging arts. Fluid reservoir 14 together with the lubricant/medicant fluid, not shown, can also be prepared as an unitized package by the foregoing methods.

In another aspect of this invention reservoir 14 and reservoir cap 15 may be combined to provide greater simplicity of use. When so combined the reservoir/cap will be pliable and sufficiently translucent or transparent so that the desired amount of lubricant/medicant fluid can be visually ascertained and applied to tampon 17. In this configuration combined reservoir/cap will engage tubular body 10, 20 so as to form a fluid seal. Thus, when the reservoir is ruptured the fluid from the reservoir will be retained within tubular body 10, 20 thereby avoiding spillage. This configuration also maintains the sterility of the tampon for the greatest period of time. That is, the sterility can be maintained until just prior to insertion into the body cavity. The combined reservoir/cap can be used with either tubular body 10 or 20.

The ability to control the amount of lubricant/medicant fluid applied to the tampon 17 is one of the advantages of the present invention. Particularly, when reservoir 14,24 has an elongated configuration the amount of fluid dispensed to and on the tampon 17 can be conveniently controlled by the amount and placement of finger pressure on the reservoir 14,24. Because the reservoir 14,24 is visible the amount of fluid applied is visually verifiable. In each instance the reservoir 14,24 can be made of a thin thermoplastic polymer, e.g. polyetheylene. The reservoir 14,24 is so fabricated that it will preferentially rupture at the mouth of the tubular body 30, 31 and tube conduits 21a,22a if present when pressure is applied.

The ability to deliver a portion of the fluid to the opposite end of the tampon via tube conduits 21a,22a, etc., or groove conduits 11a,12a,13a, etc., is another advantage of the present invention. The complete coverage of the tampon 17 facilitates the easy removal of the tampon 17 from the body cavity. Previous efforts to lubricate the tampon 17 have been directed only to the forward end of the tampon and/or inserter. The dry absorbent nature of the tampon surrounding the removal string tends to bind the mucus membrane of the body cavity wall to the tampon. Overcoming this binding effect during withdrawal of the tampon has resulted in great irritation. The present invention overcomes this problem. Depending on the actual configuration of the groove conduits 11,12,13, etc., and the fluid employed, side portions of the tampon 17 may also be treated with fluid.

When ready to use, the user removes reservoir cap 15 from the tubular body 10,20, and applies pressure to the fluid reservoir 14,24 until the reservoir 14,24 ruptures and the fluid flows on to the forward or lead end of tampon 17 the mouth of the tubular body 30,31 and down the conduits 11,12,13,21,22, etc., to treat the other end of the tampon 17. When the conduit 11, 12, 13, etc., is a groove or the like small amounts of the fluid are also applied along the length of tampon 17. In each inserter device 5,6 the end of tampon 17 ajacent plunger 16 and removal string 18 is treated with the fluid. After the desired amount of fluid is applied to tampon 17 the reservoir 14,24 with any attached conduits 21, 22, etc., or combination reservoir/cap and any loose conduits 21, 22, etc., are then discarded. When the combination reservoir/cap is used then the sequence of removing the cap and applying pressure described above is resersed and pressure is first applied to remove the desired amount of fluid and thereafter the combination reservoir/cap is discarded. The mouth of the tubular body 30,31 is then placed at the body cavity opening and the tampon inserted and used in the customary manner by pushing the tubular-like body 10,20 into the opening and pushing the plunger or piston 16 to move the tampon into place The fluid employed with devices of this invention 5, 6 can be a lubricating fluid, a medicant fluid or a combination lubricant/medicant as desired. The medicinal fluid would have the feature of medically treating the interior cavity and walls through which the tampon 17 would be placed. With the use and aid of the tampon 17 the medicant fluid can be easily applied, stays in contact with a larger surface area of the body cavity and stays in contact for a longer period of time than previously obtainable thus promoting faster and more effective treatment.

The lubricant can be any of a large number of creams, ointments and jelly currently employed to lubricate body surfaces or surgical instruments. These include polyvinyl alcohol, water soluble sterile jelly, n-vinyl pyrrolidinone preparations and the like. Sterility of the foregoing compositions can be maintained by the inclusion of minor amounts phenylmercuric salts, e.g. phenyl mercuric borate, sorbic acid, ethylenediaminetetractic acid (EDTA) and its salts and the like in amounts that are well known to those skilled in this art, e.g. 1:15,000 part ratio.

The action of the lubricant is to lubricate the tampon to make the insertion and especially the removal easier, more comfortable and painless. These features distinuguish the tampon 17 of this invention from the tampons previously described in the art. Lubricated tampon 17 can be used in the anal region to reduce irritation and make bowel movements less painful. Additionally tampon 17 may also provide comfort for the pain of hemorrids, proctitic, papillitis, cryptitis, anal fissures, incomplete fistulas, pruritis ani and relief of local pain and discomfort following anorectal surgery. The size of tampon 17 and its inserter 5, 6 can be varried as desired to more fully correspond to the size of the body cavity being treated.

The devices and methods of this invention are applicable to both the human and veterinary branches of medicine.

The foregoing devices and methods have been described in the foregoing specification for the purpose of illustration and not limitation. Many other modifications and ramifications will naturally suggest themselves to those skilled in the art based on this disclosure. These are intended to be comprehended as within the scope of the invention.

The embodiments of the invention in which an exclusive property or priviledge is claimed as defined as follows:

1. A device for placing an absorbent tampon into a body cavity comprising:
   a. an applicator body comprising a tubular-like body within which said tampon is placed, said tubular-like body containing a plurality of conduits extending longitudinally along the inner side of said tubular-like body whereby fluid for medicating and or lubricating said tampon can be conducted down the side of said tubular-like body to and on to the other end of said tampon;
   b. fluid reservoir means moveably and removeably attached to one end of said applicator body; and
   c. movement means, moveably secured within said applicator body and at the end opposite said fluid reservoir, sized and shaped to fit within said applicator body, wherein said movement means can move the tampon out of the applicator body when the device is used, whereby when said device is placed within said body cavity said treated tampon can be moved into said body cavity.

2. The device of claim 1 wherein the reservoir is a thin film container when is easily ruptured at predetermined places so that the fluid will flow to both said conduits and to the adjacent tampon.

3. The device of claim 2 wherein the reservoir is made of a thermoplastic polymer.

4. The device of claim 3 wherein the reservoir means is shielded by a rigid cap.

5. The device of claim 3 wherein the reservoir is combined with a pliable and transparent or translucent cap.

6. The device of claim 2 wherein said conduits are tubes.

7. The device of claim 2 wherein said conduits are channels formed in said tubular-like body.

8. The device of claim 2 wherein the movement means is a plunger.

9. The device of claim 2 in which the fluid is a water soluble lubricant.

10. The device of claim 2 wherein the movement means is a piston.

11. The device of claim 9 in which the fluid is a water soluble sterile jelly.

12. The device of claim 9 in which the water soluble lubricant contains a water soluble medicant.

13. The device of claim 2, in which the fluid is a water soluble medicant.

14. A method of inserting tampons into a body cavity which comprises
   (a) applying pressure to the fluid reservoir of a device which is comprised of
      (1) an applicator body comprising a tubular-like body within which said tampon is placed, said tubular-like body having a plurality of conduits extending longitudinally along the inner side of said tubular-like body whereby fluid for medicating and or lubricating said tampon can be conducted down the side of said tubular-like body to and on to the other end of said tampon;
      (2) fluid reservoir means moveably and removeably attached to one end of said applicator body; and
      (3) movement means, moveably secured within said applicator body and at the end opposite said fluid reservoir, sized and shaped to fit within said applicator body, wherein said movement means can move the tampon out of the applicator body when the device is used,
   and the desired amount of fluid flows on to the forward end of the tampon contained in said tubular-like body and through said conduits,
   (b) removing and discarding the reservoir,
   (c) placing the device at the mouth of the body cavity,
   (d) pushing the device into the body cavity and pushing said movement means to expell said tampon from said tubular body, and
   (e) removing said device.

* * * * *